US006051235A

United States Patent [19]
Theuer

[11] Patent Number: 6,051,235
[45] Date of Patent: Apr. 18, 2000

[54] GINGER-CONTAINING BABY-FOOD PREPARATION AND METHODS THEREFOR

[75] Inventor: Richard C. Theuer, Chesterfield, Mo.

[73] Assignee: Beech-Nut Nutrition Corporation, St. Louis, Mo.

[21] Appl. No.: 09/116,277

[22] Filed: Jul. 16, 1998

[51] Int. Cl.[7] ............................. A61K 35/78; A23L 1/212
[52] U.S. Cl. ......................... 424/195.1; 426/49; 424/439
[58] Field of Search ................................. 424/195.1, 439; 426/49, 615, 801

[56] References Cited

U.S. PATENT DOCUMENTS

| | | |
|---|---|---|
| 62,516 | 2/1867 | Zoeger . |
| 82,873 | 10/1868 | Ramsburgh . |
| 136,937 | 3/1873 | Putegnat . |
| 244,474 | 7/1881 | Newton et al. . |
| 256,536 | 4/1882 | Becker . |
| 276,835 | 5/1883 | Lawrence . |
| 287,602 | 10/1883 | Wilson . |
| 289,673 | 12/1883 | Litz . |
| 375,173 | 12/1887 | Marx . |
| 426,566 | 4/1890 | King . |
| 757,419 | 4/1904 | Schutz . |
| 826,990 | 7/1906 | Cartwright . |
| 4,401,683 | 8/1983 | Thompson ............................. 426/331 |
| 5,164,184 | 11/1992 | Kim ..................................... 424/195.1 |
| 5,707,630 | 1/1998 | Morrow ............................... 424/195.1 |
| 5,723,166 | 3/1998 | Theuer et al. .......................... 426/615 |

FOREIGN PATENT DOCUMENTS

| | | | |
|---|---|---|---|
| 2040563 | 1/1971 | France ............................... A23I 1/00 |
| 2-19321 | 1/1990 | Japan ............................ A61K 35/78 |

OTHER PUBLICATIONS

Eisenberg et al. What to expect the toddler years. Workman Publishing, New York. p. 596. (1994). No month found.

American Pseudo-obstruction and Hirschspring's Disease Society, Inc. (APHS), Gastroesophageal Reflux in Infants and Children (3 pages) No date given.

Awang, Ginger, Canadian Pharmaceutical Journal125:309-311 (Jul. 1992).

Backon, Ginger as an antiemetic: possible side effects due to its thromboxane synthetase activity, Anaesthesia 46(8):705–706 (1991).

Backon, Ginger in preventing nausea and vomiting of pregnancy: a caveat due to its thromboxane synthetase activity and effect on testosterone binding, European J. of Obsterics & Gynecology and Reproductive Biology 42:163–164 (1991).

Forsyth et al., Mothers' Perceptions of Problems of Feeding and Crying Behaviors, Amer. J. Dis. Childr. 139:269–273 (Mar. 1985).

Grauds, Ginger (Zingiber Officinale), Pharmacy Times 61:50 (Nov. 1995).

Liu, Ginger root, a new antiemetic, Anaesthesia 45(12):1085 (1991).

Monographs on the Medicinal Uses of Plant Drugs, European Scientific Cooperative on Phytotherapy pp. 1–7 (1996).

Murray, Chapter 12 Ginger, The Healing Power of Herbs Prima Publishing, Rocklin, CA pp. 132–142 (1995).

Nelson et al., Prevalence of Symptoms of Gastroesophageal Reflux During Infancy, Arch pediatr. Adolesc. Med. 151:569–572 (Jun. 1997).

Pinco et al., Citizen Petition to Amend FDA's Monograph on Antiemetic Drug Products for Over-the-Counter ("OTC") Human Use to Include Ginger, European–American Phytomedicines Coalition, May 26, 1995, 33 pages.

Wentz, How to evaluate gastroesophageal reflux, Infectious Dis. Childr., pp. 40, 42 No date given.

Wichtl et al., Zingiberis Rhizoma, Heral Drugs and Phytopharmaceuticals, N. G. Bisset ed. Medpharm, Stuttgart pp. 537–539 (1994).

Wood et al., Zingiber, The Dispensatory of The United States of America, 22nd Ed, J. B. Lippincott Company, Philadelphia pp. 495, 1073–1074, 141 and 1208–1211 (1937).

Wood et al., Comparison of Efficacy of Ginger with Various Antimotion Sickness Drugs, Clin. Research Practices & Drug Reg. Affairs 6(2):129–136 (1988).

Yamahara et al., Inhibition of Cytotoxic Drug–Induced Vomiting in Suncus by a Ginger Constituent, J. of Ethnopharmacology 27:353–355 (1989).

Ashbrook et al., Infants' Acceptance of Strong– and Mild–Flavored Vegetables, J. Nutrition Ed., 17:5, 6, 46 (1985).

Beal, On the Acceptance of Solid Foods, and other Food Patterns, of Infants and Children, Pediatrics, 20:448–456 (Sep. 1957).

Bone, et al., Ginger–root—a new antiemetic, The effect of ginger root on postoperative nausea and vomiting after major gynaecological surgery, Anaesthesia, 45:669–671 (1990).

Conlin, Oral Ingestion of Encapsulated Ginger and Reported Self–Care Actions for the Relief of Chemotherapy–Associated Nausea and Vomiting, Dissertation Abstr. Intl., 47:3297B (1987).

Dollery, Therapeutic Drugs, Churchill Livingston, N.Y., pp. M148–152 (1991).

Fischer–Rasmussen, Ginger treatment of hyperemesis gravidarum, Europ. J. Obstet. & Gynecol. and Reprod. Bio., 38:19–24 (1990).

Forfar and Arneil's Textbook of Pediatrics Fifth Ed., Campbell and McIntosh, Eds., Churchill Livingston, N.Y., pp. 427–428.

Glassman et al., Gastroesophageal Reflux in Children, Gastroenterology Clinics of North America, 24:71–98 (Mar. 1995).

Govindarijan, CRC Crit. Rev. in Food Sci. and Nutr., 17:1–96 (1982).

(List continued on next page.)

Primary Examiner—Michael P. Woodward
Assistant Examiner—Marjorie A Moran
Attorney, Agent, or Firm—Armstrong Teasdale LLP

[57] ABSTRACT

Baby-food compositions containing ginger which can be used in reducing gastroesophageal reflux in infants are disclosed. The compositions can contain a ginger puree and one or more fruits or vegetables. Also disclosed are methods of making and using the compositions.

21 Claims, No Drawings

OTHER PUBLICATIONS

Govindarajan, *CRC Crit. Rev. in Food Sci. and Nutr.*, 17:189–258 (1983).

Grontved et al., Ginger Root Against Seasickness, *Acta Otolaryngol* (*Stockh*), 105:45–49 (1988).

Grontved et al., Vertigo–Reducing Effect of Ginger Root, *ORL*, 48:282–286 (1986).

Holtmann et al., The Anti–motion Sickness Mechanism of Ginger, *Acta Otolaryngol* (*Stockh*), 108:168–174 (1989).

Kajiura et al., Early Developmental Change in Bitter Taste Responses in Human Infants, *Developmental Psychobiology* 25(5):375–386 (1992).

Kasahara et al., Pharmacological Actions of Pinellia Tubers and Zingiber Rhizomes, *Shoyakugaku Zasshi*, 37(1):73–83 (1983).

Killeen, *Advance for Physician Assistants*, pp. 15–16, 17 (Jun., 1997).

Landis, *Herbal Defense*, Warner Books, Inc., N.Y., p. 255 (1997).

Lowenberg, Development of Food Patterns in Young Children, *Nutrition in Infancy and Childhood*, 165–180 (1995).

Lumb, *Anaesthesia*, 48(12):1118 (Dec. 1993).

Mowrey et al., Motion Sickness, Ginger, and Psychophysics, *Lancet*, pp. 655–657 (Mar. 1982).

Nelson, *Textbook of Pediatrics, 15th Ed.*, Nelson, Ed., Saunders Co., pp. 1055–1056 (1996).

Phillips et al., *Zingiber officinale* does not affect gastric emptying rate, *Anaesthesia*, 48:393–395 (1993).

Phillips et al., *Zingiber officinale* (Ginger)—an antiemetic for day case surgery, *Anaesthesia*, 48:715–717 (1993).

Rosenstein et al., Differential Facial Responses to Four Basic Tastes in Newborns, *Child Develop.*, 59:1555–1568 (1988).

Schmid et al., Comparison of Seven Commonly Used Agents for Prophylaxis of Seasickness, *J. Travel Med.*, 1:203–206 (1994).

Trahms, Factors that Shape Food Patterns in Young Children, *Nutrition in Infancy and Childhood*, 181–194 (1993).

Yamahara et al., Active Components of Ginger Exhibiting Anti–serotonergic Action, *Phytotherapy Research*, 3(2):70–71 (1989).

Yamahara et al., Gastrointestinal Motility Enhancing Effect of Ginger and Its Active Constituents, *Chem. Pharm. Bull*, 38(2):430–431 (1990).

Mehta, S.M. Indian Medical Gazette, 119 (1), pp. 20–21. (Jan. 1985).

GINGER-CONTAINING BABY-FOOD PREPARATION AND METHODS THEREFOR

BACKGROUND OF THE INVENTION

(1) Field Of The Invention

This invention relates generally to baby-food compositions and, more particularly, to novel baby-food compositions comprising ginger and to methods of making and using the compositions.

(2) Description Of The Related Art

Gastroesophageal reflux is the passive regurgitation of gastric contents into the esophagus, often manifested in infants as the "spitting up" of milk. (*Forfar and Arneil's Textbook of Pediatrics Fifth Ed.*, Campbell and McIntosh, Eds., Churchill Livingstone, N.Y., pp 427–428). This condition is distinctly different from vomiting, which is an active process that requires the contraction of the diaphragm and abdominal muscles to initiate the event (id.).

Although the lower esophageal sphincter functions to prevent reflux of gastric contents into the esophagus, gastroesophageal reflux is known to be a physiological phenomenon occurring occasionally in all individuals during postprandial periods (Glassman et al., *Gastrenterol. Clin. N. Amer.* 24:71–98, 1995). Gastrointestinal reflux is particularly common in children and it can sometimes be a problem when associated with an incompetent or, in the case of infants, an immature lower esophageal sphincter (*Nelson Textbook of Pediatrics, 15th Ed.*, Nelson, Ed., Saunders Co., 1996, pp 1055–1056). Nevertheless, regurgitation or "spitting up" often resolves with maturity. (Id.).

The majority of infants have minor degrees of reflux and this is accepted by most caregivers as being a normal, although sometimes inconvenient feature of infancy. However, inexperienced or stressed caregivers may have difficulty coping with the problem. Furthermore, in some infants, significant reflux occurs associated with complications such as esophagitis, aspiration or failure to thrive (*Forfar and Arneil's Textbook of Pediatrics Fifth Ed.*, supra).

The particular approach used in dealing with gastroesophageal reflux depends upon the severity of symptoms. (Killeen, *Advance for Physician Assistants* June 1997; *Forfar and Arneil's Textbook of Pediatrics Fifth Ed.*, supra; *Nelson Textbook of Pediatrics, 15th Ed.*, supra). With mild to moderate reflux, the infant can be kept prone or with the head raised in bed. Dietary changes such as thickening the infant's formula with cereal can also be used.

Where simpler measures fail to reduce the reflux, pharmaceutical treatments are sometimes used including the use of prokinetic agents or drugs that increase gastric pH (*Forfar and Arneil's Textbook of Pediatrics, Fifth Ed.*, supra; Killeen, *Advances for Physician Assistants*, supra). The prokinetic agents increase gastric emptying and esophageal motility along with lower esophageal sphincter pressure. Drugs that increase gastric emptying, esophageal motility and lower esophageal sphincter pressure include metoclopramide (*Therapeutic Drugs*, Dollery, ed., Churchill Livingston, N.Y., 1991, pp. M148–152), domperidone and cisapride (*Forfar and Arneil's Textbook of Pediatrics, Fifth Ed.*, supra). Drugs that increase gastric pH include histamine H-2 receptor blocking drugs such as cimetidine or ranitidine and proton pump inhibitors such as omeprazole (id.). All of these drug treatments, however, have the potential of producing undesirable side effects.

Ginger is the rhizome of the plant *Zingiber officinale*. Ginger is a commonly used spice which exhibits a characteristic aroma and mild pungency both of which contribute to the flavor of ginger. Ginger contains volatile aromatic oils referred to as essential oils, which are largely responsible for the aroma of ginger; pungent compounds which make up the solvent extractable oleoresins in addition to the essential oils and which are largely responsible for the pungent flavor of ginger; and starch, proteins and other substances (Govindarijan, *CRC Crit. Rev. in Food Sci. and Nutr.* 17:1–96, 1982). In addition to its common usage as a spice in the dried and ground form, ginger has been shown to relieve nausea and vomiting associated with a number of conditions including nausea and vomiting in pregnant women (Fischer-Rasmussen et al, Europ. J Obstetrics & Gynocol and Reprod Biology 38:19–24, 1990), in motion sickness (Grontved et al., *ORL* 48:282–286, 1986; Grontved et al., *Acta Otolaryngol (Stockh)* 105:45–49, 1988; Holtman et al, *Acta Otolaryngol (Stockh)* 108:168–174, 1989; Mowery et al, *Lancet* Mar. 20, 1982; Schmid et al, *J Travel Med* 1:203–206), in the postoperative setting (Phillips et al. *Anaesthesia* 48:715–717, 1993) and in chemotherapy-associated nausea and vomiting (Conlin, *Dissertation Abstr. Intl.* 47:3297B, 1987). The mechanism of this antiemetic action of ginger is unknown although both a local effect on the gastrointestinal tract (Holtmann et al, *Acta Otolaryngol* 108:168–174, 1989) and a central action (Lumb, *Anaesthesia* 48:1118, 1993) have been proposed. All of these earlier studies dealt with nausea and vomiting which as noted above are distinctly different conditions than gastroesophageal reflux and none of the reports provided any suggestion as to whether ginger might be useful in relieving gastroesophageal reflux.

The pharmacologic effects of ginger have also been studied and one report has indicated that ginger root extracts, i.e. oleoresin components, increase gastrointestinal motility following oral administration (Yamahara et al, Chem Pharm Bull., 38: 430–431, 1990; Kasahara et al, Shoyakugaku Zasshi 37:73, 1983). This effect would appear to have been due predominantly to an increase in intestinal motility inasmuch as it has been reported that ginger powder does not affect gastric motility or gastric emptying rate (Phillips et al, *Anaesthesia* 48:393–395, 1993).

Ginger has been suggested for use in indigestion in adults. Although ginger is generally recognized as safe by the U.S. Food and Drug Administration (21 C.F.R. § 182.1), nevertheless, ginger is, in general, not used in infants as a result of its spicy, intense character (see, for example, Landis in *Herbal Defense*, Warner Books, Inc., N.Y., 1997, p. 255). Thus, there remains a continuing need to develop for a safe and effective approach to relieving gastroesophageal reflux in babies.

BRIEF DESCRIPTION OF THE INVENTION

Accordingly, the inventor herein has succeeded in discovering that certain ginger-containing compositions can be prepared in acceptable baby-food formulations for use in reducing gastroesophageal reflux in an infant. Thus, in one embodiment, the present invention involves a method for reducing gastroesophageal reflux in an infant. The method comprises feeding to the infant the ginger-containing composition in an amount sufficient to diminish gastroesophageal reflux. The composition containing ginger is in an acceptable baby-food formulation. In one version of this embodiment, the ginger can be in the form of a blanched ginger puree. Such baby-food compositions preferably contain from about 0.01% to about 1% (w/w) of the blanched ginger puree and more preferably, from about 0.1% to about 0.5% (w/w). The composition can, in addition to the ginger, contain one or more fruits or vegetables which are, preferably, in a shredded, grated, chopped, comminuted or pureed form. Because the baby-food compositions of the present invention are comprised of a pureed ginger rhizome, the compositions in such embodiments are whole food preparations. Furthermore, ginger has been used by humans for 2,500 years and it is generally recognized as safe by the U.S. Food and Drug Administration as are the essential oils and oleoresins of ginger (21 C.F.R. §182.1).

The present invention, in another embodiment, comprises a baby-food composition containing blanched ginger puree. The baby-food composition containing ginger puree is in an acceptable baby-food formulation which preferably contains from about 0.01% to about 1% of the blanched ginger puree and more preferably, from about 0.1% to about 0.5% ginger (w/w). The ginger-containing composition can also contain one or more fruits or vegetables.

In another embodiment, the present invention involves a method for manufacturing a baby-food product. The method comprises preparing a composition containing a blanched ginger puree. The ginger-containing composition is prepared in an acceptable baby-food formulation, preferably, containing from about 0.01% to about 1% of the blanched ginger puree and more preferably, from about 0.1% to about 0.5% (w/w). The ginger-containing composition can also contain one or more fruits or vegetables.

Among the several advantages achieved by the present invention, therefore, may be noted the provision of baby-food compositions which are capable of diminishing gastroesophageal reflux in an infant; the provision of a method for diminishing gastroesophageal reflux by feeding to an infant the baby-food compositions of the present invention; the provision of compositions and methods for decreasing the regurgitation or "spitting up" of liquids by the infant; and the provision of methods for manufacturing baby-food compositions for use in diminishing gastroesophageal reflux in babies.

DETAILED DESCRIPTION OF THE INVENTION

In accordance with the present invention, it has been discovered that ginger can be incorporated into an acceptable baby-food composition which can be used to improve the health of the infant and, in particular, to diminish gastroesophageal reflux. The term baby as used herein is intended to mean a child in the first period of life generally considered to be in the age range of from birth to about four years and to include infants, i.e. babies from birth to 12 months as well as toddlers. An acceptable baby-food composition is intended to encompass semi-solid food preparations designed for feeding to a baby and meeting all of the regulatory and organoleptic requirements for such compositions. Although designed as baby-food compositions and referenced as such herein, the compositions within the present invention can, of course, be consumed by other population groups such as by individuals who are sick or those who have special nutritional requirements and, in particular, by geriatric individuals so long as the compositions are in an acceptable baby-food formulation. Furthermore, the compositions within the present invention can be used in such other population groups in addition to infants to relieve gastroesophageal reflux.

The baby-food compositions of the present invention are prepared to contain ginger. Ginger rhizome also referenced as ginger root can be processed in a number of ways for incorporation into the baby-food preparations herein. For example, following cleaning, the ginger rhizome can be either peeled or unpeeled followed by air drying and grinding or steaming, drying, and grinding. Preferably, however, the ginger to be incorporated into the baby-food preparations of the present invention are in the "fresh" form of ginger rhizone as a whole food. This whole food concept involves minimal preparation of components of the baby-food composition such as by cleaning, peeling, comminuting or pureeing and heating the components as distinguished from further processing of the components which is less preferable. Such further processing can involve, for example, treatment of a component by drying and milling into a flour, bleaching, treatment with solvents to remove undesirable components or to obtain extracts, and the like.

Preferably the unpeeled ginger rhizome is cleaned, blanched and pureed in preparation for use. The blanching can be accomplished by scalding or parboiling in water or by steaming the ginger to an internal temperature of at least about 160° F. (71° C.) or greater. This can be done, for example, by simmering in water at a temperature of about 190° to about 210° F. for about 10 minutes.

The blanched ginger can then be pureed, for example, by using a blender in preparation for combining with other components of the baby-food composition. Such pureed forms of ginger can be stored in frozen form or pasteurized into a shelf-stable form for later use. Pasteurization can involve subjecting an acidified puree to a heat of 180° F. (82° C.) for about 3 minutes. Blanched "fresh" ginger rhizome in the form of a frozen or pasteurized puree can be obtained commercially (Tradewind Farms, Inc., Visalia, Calif. 93291).

The ginger component of the baby-food composition of the present invention contains an amount of ginger suitable for diminishing gastroesophageal reflux. Preferably, the composition will contain from about 0.01% to about 1% (w/w) of the blanched ginger puree and more preferably, from about 0.1% to about 0.5% (w/w). The term "about" as used herein is intended to included variances of 0.05 percentage values above and below indicated values so that about 0.5% is intended to mean from 0.45% to 0.55%. The amounts of ginger that produce beneficial effects in nausea in vomiting in adults have been reported to be in the range of from 250 mg to 1 gram of dried ginger powder (see for example, Fischer-Rasmussen et al, *Europ. J. Obstet. & Gynecol. and Reproduct. Biol.* 38:19–24, 1990; Bone et al. *Anaesthesia* 45:669–671, 1990; Grontved et al., *Acta Otolaryngol* (*Stockh*) 105:45–49, 1988). Whereas an adult would be expected to have a body mass of about 70 kg, an infant has a body mass of about 3.5 kg at birth and about 7.0 kg at 6 months. Thus, based on body mass differences one would predict that 250 mg to 1 gram amounts in an adult would be equivalent to about 12.5 to 50 mg in a newborn and 25 to 100 mg in an infant of 6 months. Furthermore, fresh or "green" ginger yields approximately 20% ginger upon drying (Govindarajan, supra) so that 1 gram of dried ginger powder is roughly equivalent to 5 grams of fresh ginger. Thus, one would expect that effective amounts of fresh ginger in a newborn would be about 62.5 mg to about 250 mg and that in an infant of 6 months would be from about 125 mg to about 500 mg. A typical jar of commercial baby food for six-month-old infants contains four ounces or 113 grams of baby-food composition. Assuming that 100 grams of the baby-food composition is consumed, the range of effective amounts would be expected to be from about 71 mg to about 565 mg per jar or from 0.0625%, i.e. about 0.1%, to about 0.5% fresh ginger puree. Where forms of ginger other than blanched ginger puree are used in further embodiments of the present invention, the skilled artisan can readily calculate the equivalent amount of ginger needed in the formulation.

Different forms of ginger other than the "fresh" pureed preparations can also be use in a baby-food preparation so long as the preparation is in an acceptable baby-food formulation. The powdered, dried ginger can in some instances lose some of the essential oils during the drying process. Furthermore, gingerol, which is the primary oleoresin component of fresh ginger and the prominent pungent flavor component in ginger, is typically degraded chemically in a dehydration reaction during the drying process or in subsequent storage to form shogaol. Thus, whereas in fresh ginger the oleoresin component contains predominantly gingerol and little shogaol, dried and stored ginger products contain large amounts of shogaols. Nevertheless, both gingerol and shogaol have been shown to produce an antiemetic effect in animals (Yamahara et al *Phytotherapy Research* 2:70–71, 1989). It is, therefore, believed that dried ginger can also be used in the baby-food formulation of the present invention.

General reference to ginger herein is intended to encompass all forms of ginger including fresh ginger, dried and ground ginger, and ginger oleoresin or ginger extract obtained by extraction of the fresh rhizome with alcohol, acetone or other solvent.

The volatile oil component of fresh ginger rhizome contains citrals, which is the class name for terpenoid compounds including geraniol, limonene and niral. Govindarajan, supra. These substances are not present in the dried rhizome because they are reportedly lost during the drying process. The citrals appear to be responsible for the citrus, lemony aroma and flavor considered characteristic of freshly cut or grated ginger. Nevertheless, the citrus, lemony character of fresh ginger is less desirable for use in a baby-food preparation because this imparts a sharp, bitter flavor with lemony after-taste to the composition. Accordingly in some embodiments in which citrals are present it can be desirable to add further components which can balance the aroma and flavor of the citrals. However, refined sugar should not be added for this purpose in view of recommendations of the U.S. Departments of Agriculture and Health, Education and Welfare to not add sugar to baby food (*Nutrition and Your Health. Dietary Guidelines for Americans,* 1980).

Additional substances which can be added to the baby-food preparation of the present invention to balance any citrus, lemony flavor, include fruits or vegetables which are prepared in a suitable form such as by shredding, grating, chopping, comminuting or pureeing the fruit or vegetable. Examples of fruits that can be incorporated in prepared form include apple, guava, papaya, pineapple, raspberry, strawberry, grape, grapefruit, cherry, orange, banana, pear, cranberry, blueberry, peach, olive, coconut, blackberry, mulberry, fig, prune, lemon, lime, date, pomegranate, apricot, mango, avocados, kiwi, nectarine, raisins, plum, and combinations thereof.

Vegetables which can be incorporated in prepared form can include buckwheat, rhubarb, sorrel, beets, spinach, Swiss chard, cantaloupe, casaba, cucumber honeydew, pumpkin, summer squash, winter squash, watermelon, barley, corn, hominy, millet, oat, rice, rye, sorghum, sugar cane, wheat, aloe, asparagus, chives, garlic, leek, onion, sarsaparilla, shallot, cottonseed, marshmallow, okra, sweet potato, broccoli, brussel sprouts, cabbage, cauliflower, collards, garden cress, horseradish, kale, kohlrabi, mustard, radish, rutabaga, turnip, watercress, bell pepper, cayenne pepper, paprika, eggplant, white potato, tomato, anise, caraway, carrot, celeriac, celery, coriander, dill, fennel, parsley, parsnip, acacia, alfalfa, black-eyed pea, broad bean, carob bean, chick pea, common beans, green beans, lentil, licorice, lima bean, mesquite, pea, peanut, tamarind, tragacanth, and combinations thereof.

Although less preferable than whole food components, additional filler substances such as corn starch, rice flour, wheat flour, nonfat dry milk and the like can be included in certain embodiments of the composition.

The ginger-containing compositions of the present invention are in acceptable baby-food formulations. The terms acceptable baby-food formulation are used interchangeable herein with the terms acceptable baby-food composition and acceptable baby-food preparation. An acceptable baby-food formulation is one suitable for feeding to a baby and included within the meaning of the terms acceptable baby-food formulation is any regulatory agency requirements for foods intended for consumption by infants. For example, lactic acid and malic acid have been reviewed by the Food and Drug Administration and determined not to be generally recognized as safe for use in foods for infants (see 21 C.F.R. §184.1061, §184.1069). Thus, these acids would not be incorporated into an acceptable baby-food formulation. On the other hand, the use of citric acid and phosphoric acid have been determined to be generally recognized as safe. (see 21 C.F.R. §184.1033, §182.1073). Therefore, these acids can be incorporated into an acceptable baby-food formulation. In this regard, ginger is generally recognized as safe by the U.S. Food and Drug Administration as are the essential oils and oleoresins of ginger (21 C.F.R. §182.1) and as such any of these can be safely incorporated into the baby-food composition.

An acceptable baby-food formulation is also a formulation whose overall combination of organoleptic characteristics, i.e., taste, mouthfeel/texture, odor and color/appearance is of such a nature that the infant will consume and not reject the formulation and the caregiver will serve the formulation to the infant. For example, infants are known to display an aversion to bitter tastes at a very early age and to strong flavors such as can be present in some vegetables. (Trahms, in *Nutrition in Infancy and Childhood,* Pipes and Trahms, Eds, Mosby, St. Louis, 1993, pp. 181–194; Kajiura et al, *Developmental Psychobiol* 25:375–386; Rosenstein et al., *Child Develop* 59:1555–1568, 1988; Lowenberg, in *Nutrition in Infancy and Childhood,* Pipes and Trahms, Eds, Mosby, St. Louis, 1993, pp. 165–180; Brooks, supra; Lawless, supra; Ashbrook et al, *J Nutrition Ed* 17:5, 6, 46, 1985; Beal *Pediatrics* 20:448–456, 1957). Therefore, an acceptable formulation of a baby-food composition does not have a strong bitter taste or a strong flavor such as can be present in some vegetable preparations. In general, it is recommended that ginger not be given to babies as a result of its spicy, intense character (see, for example, Landis in *Herbal Defense,* Warner Books, Inc., New York, 1997, p. 255). Therefore, an acceptable baby-food preparation containing ginger would be in a formulation that does not exhibit an objectionable spicy and intense character.

Thus, it is desirable to minimize the strong aromas and flavors normally present in fresh ginger. In one preferred embodiment this is accomplished by blanching the fresh ginger and combining the pureed, blanched ginger with a fruit or vegetable. It will be readily apparent to the skilled artisan that other approaches can be used to diminish the strong aromas and flavors of the fresh ginger. For example, although it is not intended that this invention be bound by any theory, it is believed that the volatile ginger oil contributes to the strong aroma and flavor of fresh ginger but contributes little or nothing to the diminishing effect of ginger on gastroesophageal reflux. Therefore, one approach to decreasing the strong aroma and flavor would be to freeze dry the fresh ginger so as to eliminate the volatile ginger oils without altering the nonvolatile components of the fresh ginger.

An acceptable baby-food formulation will also have a texture that is acceptable to the baby. For example, foods that are too dry or gritty are usually unacceptable to infants. In general, acceptable baby-food formulations will be smooth in texture. In addition, younger infants typically prefer food that is soft and homogenous. For older infants, however, a nonhomogenous texture may be desired. Because of such preferences, baby foods are typically produced in different forms, depending on the age of the intended consumer. For example, Beech-Nut Stage 1 products are intended to be consumed by infants from about three months of age. Beech-Nut Stage 2 products, which are strained and will pass through a 0.50 orifice, are intended to be consumed by infants from about six months of age. Infants of about nine months of age and older are the intended consumers of Beech-Nut Stage 3 Junior products, which have chunky components that will pass through a ⅜ inch screen.

Preferably, the desired texture is achieved using the whole food concept by mixing whole food components having the desired texture. Moreover, the color and appearance of the formulation are such that the infant or the adult caregiver will not reject the formulation. Acceptable colors tend to be light rather than dark. Preferably, acceptable color is achieved using the whole food concept in which food components are added which produce the desired color for the overall mixture. The appearance of the formulation should also be smooth and homogenous.

In addition, the composition should not produce adverse side effects such as acid indigestion, diarrhea, allergic responses or the like.

Testing a baby-food composition for organoleptic acceptability can be readily performed by the skilled artisan using routine methods such as those described in the Examples below. For example, since the adult perception of bitter tastes closely follows that in the infant (Lawless, *J. Am. Diet. Assoc.* 85:577–585, 1985) and since food preferences or aversions of the adult caring for the infant are known to influence which foods are offered to the infant (Trahms, in *Nutrition in Infancy and Childhood,* Pipes and Trahms, Eds, Mosby, St. Louis, 1993, pp. 181–194; Brooks, The *Wall St J,* Dec. 4, 1996 pp A1, A6), it is possible to conduct acceptability testing in adults. Standard testing procedures for sensory evaluation are known in the art (see, for example, Stone and Sidel in *Sensory Evaluation Practices,* Academic Press, Orlando, 1985, pp 58–86, 227–252).

Testing for organoleptic acceptability in infants could be conducted, for example, after obtaining informed consent from parents in a double-blind, randomized controlled study. Infants of ages from about 4 months to about 12 months would be fed a series of baby-food compositions prepared containing, for example, 0.5% ginger or a reference baby-food preparation known to be accepted by the infants such a commercially available baby food of similar composition but not containing ginger. The adult feeding the infant would then record acceptability and tolerance including amount offered, amount consumed and amount refused by the babies. Acceptability rating would be performed by methodology known in the art (for example, Stone and Sidel, supra). The results would be analyzed and compositions showing acceptance comparable to or greater than that of the reference baby food would be considered organoleptically suitable for use as an infant food.

INDUSTRIAL APPLICATION

The baby-food compositions of the present invention have application for use as semi-solid preparations for infants. In particular, the compositions and methods can be used to diminish gastroesophageal reflux. This can serve relieve the inconvenience of the infant spitting up and assist caregivers that may be inexperienced or stressed in coping with the spitting. Furthermore, use of the compositions can also improve the health of the infant, in particular, in infants where regurgitation would otherwise be significant and, as a consequence, the infant might be at risk for developing esophagitis, aspiration or failure to thrive due to poor weight gain. Moreover, the ginger-containing compositions of the present invention can also be used to avoid nausea and vomiting and restore normal gastric and esophageal function in infants as has been reported for ginger in adults.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example illustrates the preparation of baby-food compositions containing varying amounts of fresh, uncooked ginger blended with applesauce.

Fresh ginger was obtained from local grocery stores and washed and chopped into small pieces. The chopped fresh ginger was blended in a home blender with varying amounts of commercially obtained, unsweetened applesauce to prepare mixtures containing 4%, 3%, 1.89% or 1% ginger. The samples were tasted and the flavor profiles of the mixtures determined as shown in Table 1.

TABLE 1

| Ginger level | Flavor Evaluation |
| --- | --- |
| 4% | unpleasant: acrid, burning, lingering sharp citrusy aftertaste |
| 3% | unpleasant: burning taste |
| 1.89% | unpleasant: strong taste of ginger; no apple notes |
| 1% | not bad: ginger flavor still obscures apple notes |
| 0% | thin, unsweetened applesauce taste |

Thus, the level of 1% fresh ginger puree combined with an applesauce yielded a palatable composition whereas fresh ginger at higher levels, i.e. 1.89% and greater, yielded a composition with a strong, unpleasant aftertaste.

EXAMPLE 2

This example illustrates the preliminary preparation and testing of compositions containing blanched fresh ginger mixed with pear puree or sweet potato puree to determine the taste profile of the compositions.

Fresh ginger was cooked prior to mixing with fruit puree to test the effect of blanching on the taste profile of the composition. Whole "hands" of fresh ginger were cleaned and placed in simmering water at about 190° F. to about 210°

F. for about ten minutes. The internal temperature of the ginger was then measured and determined to be in excess of 160° F.

Blanched fresh ginger and unblanched fresh ginger were chopped into small pieces and then blended either with pear baby-food puree or sweet potato baby-food puree at a concentration of 1% ginger puree Comparison of the taste profiles of the mixtures of blanched and unblanched ginger with either pear puree or sweet potato puree revealed that the mixtures made with cooked fresh ginger had less of the fresh ginger afterbite/astringency/citrus/lemony flavor notes than mixtures made with uncooked fresh ginger rhizome.

Thus, blanching fresh ginger prior to blending to form a puree with apple puree or sweet potato puree yields a composition with a mild flavor having less bite and citrus, lemony flavor and aftertaste than mixtures tested in Example 1.

EXAMPLE 3

This example illustrates the preliminary preparation and taste testing of a composition containing a Yellow Stone carrot puree and blanched ginger.

Sample TK181A

Yellow Stone carrots were prepared by washing and peeling, and then cut into dices and frozen. Two thousand five hundred grams of frozen Yellow Stone carrot dices were cooked in a pressure cooker at 15 p.s.i.g. for five minutes. The cooked dices were then placed in a food blender, 375 grams of water were added and the carrots and water were blended until smooth.

One kilogram of the puree was then weighed. Portions at a temperature of 150° F. were placed in 4-oz. glass jars and further processed in a conventional fashion and as further required by 21 C.F.R. §113 et seq., "Thermally Processed Low-Acid Foods Packaged in Hermetically Sealed Containers," which is incorporated herein by reference. The sample was identified as TK181A.

Sample TK181B

Nine hundred and ninety grams of carrot puree were weighed into a container. Frozen, blanched unpeeled ginger puree was obtained commercially (Tradewind Farms, Inc., Visalia, Calif. 93291) and thawed. Ten grams of the thawed ginger puree were mixed with the carrot puree. Portions at a temperature of 150° F. were placed in 4-oz. glass jars and further processed in a conventional fashion and as further required by 21 C.F.R. §113 et seq.

Both the TK181A and TK181B samples were tasted to determine the taste profile. TK181A, which contained no ginger, had a mild, slightly sweet carrot taste. TK181B, which contained 1% blanched ginger puree, had a noticeable citrusy flavor which is typical of ginger. The taste of TK181B was liked by adult taste testers who like the taste of ginger.

EXAMPLE 4

This example illustrates the preparation and taste testing of blanched and unblanched ginger puree mixed at levels of 1% or 2% with apple puree.

Samples TK185A (1% Blanched Ginger)

Blanched ginger root puree was prepared as described in Example 2. After heating in hot water, the ginger was removed and the internal temperature determined to be 165° F. The blanched ginger root was then cut into chunks, placed in a blender and made into a smooth puree.

Fresh Golden Delicious apples were peeled, cored, blanched, blended into a puree, and frozen until needed. Nine hundred and ninety grams of thawed Golden Delicious apple puree were weighed into a double-boiler container and heated to 160° F. to 180° F. Ten grams of blanched ginger puree were mixed with the apple puree to produce a composition containing 1% blanched ginger puree. Portions were placed in 4 ounce glass jars and hot-packed using a microwave oven in a conventional fashion and as further required by 21 C.F.R. § 114 et seq., "Acidified Foods," which is incorporated herein by reference. The pH of the mixture was 3.70 prior to processing and 3.68 after processing. The resulting composition was coded TK185A.

Sample TK185B (1% Unblanched Ginger)

Fresh ginger root was washed with water and then cut into chunks. The chunks were placed in a blender and made into a smooth puree.

Nine hundred and ninety grams of apple puree were weighed into a double-boiler container and heated to 160° F. to 180° F. Ten grams of the unblanched ginger puree were then mixed with the apple puree to produce a composition containing 1% unblanched ginger puree. Portions were placed in 4 ounce glass jars and hot-packed using a microwave oven in a conventional fashion and as further required by 21 C.F.R. §114 et seq. The pH of the mixture was 3.69 prior to processing and 3.68 after processing. The resulting composition was coded TK185B.

Sample TK185C (2% Blanched Ginger)

Nine hundred ninety grams of heated apple puree and 20 grams of blanched ginger puree were mixed to produce a 2% blanched ginger puree composition. Portions were placed in 4 ounce glass jars and hot-packed using a microwave oven in a conventional fashion and as further required by 21 C.F.R. §114 et seq. The pH of the mixture was 3.75 prior to processing and 3.73 after processing. The resulting composition was coded TK185C.

Sample TK185D (2% Unblanched Ginger)

Nine hundred ninety grams of heated apple puree and 20 grams of unblanched ginger puree to produce a 2% ginger puree composition. Portions were placed in 4 ounce glass jars and hot-packed using as microwave oven in a conventional fashion and a further required by 21 C.F.R. §114 et seq. The pH of the mixture was 3.73 prior to processing and 3.71 after processing. The resulting composition was coded TK185C.

Taste Testing of Samples

Eleven evaluators experienced in tasting baby food, separately evaluated the samples on a blinded basis. They preferred TK185A with 1% blanched ginger although many of the taste testers did not like this composition. The 1% unblanched ginger sample (TK185B) and the two 2% ginger samples were noted by some to have a strong bite.

EXAMPLE 5

This example illustrates the preparation and taste testing of compositions containing 0.1%, 0.2%, and 0.5% blanched ginger puree combined with apple puree.

Sample TK185A containing 1% blanched ginger puree was prepared as described in Example 4.

Sample HK8707A (0.5% Blanched)

One hundred fifty-one grams of Beech-Nut Stage 1 Golden Delicious Applesauce were weighed into a container and combined with 50.2 grams of the product TK185C of Example 4 containing 2% blanched ginger. After mixing, samples were transferred into glass jars, refrigerated overnight and subjected to organoleptic evaluation the following day.

Sample HK8707B (0.2% Blanched)

One hundred and eighty grams of Golden Delicious Applesauce were weighed into a container and combined with 20.1 grams of product TK185C of Example 4 which contained 2% blanched ginger. After mixing, samples were transferred into glass jars, refrigerated overnight and subjected to organoleptic evaluation the following day.

Sample HK8707C (0.1% Blanched)

One hundred ninety grams of Golden Delicious Applesauce were weighed into a container and combined with 10.0 grams of product TK185C of Example 4 containing 2% blanched ginger. After mixing, samples were transferred into glass jars, refrigerated overnight and subjected to organoleptic evaluation the following day.

Sample HK8707D (Control)

One unopened jar of Beech-Nut Stage 1 Golden Delicious Applesauce of the same lot code used to make the above samples was coded as HK8707D, refrigerated overnight and subjected to organoleptic evaluation the following day.

The samples HK8707A, B, C, D and TK185A were identified only by a nonsense blinded letter code. Ten individuals familiar with baby food were asked to taste these samples and to indicate if spice was present or not. Answers that could be interpreted as Yes, No or Maybe were used. The results are shown in Table 3.

TABLE 2

| Sample | Ginger level | YES | NO | MAYBE |
| --- | --- | --- | --- | --- |
| TK185A | 1% | 6 | 0 | 1 |
| HK8707A | 0.5% | 7 | 1 | 0 |
| HK8707B | 0.2% | 0 | 7 | 0 |
| HK8707C | 0.1% | 0 | 7 | 0 |
| HK8707D | 0% | 0 | 5 | 1 |

Thus, compositions containing 0.1% and 0.2% blanched ginger puree in applesauce exhibited no detectable spice flavor whereas 0.5% and 1% blanched ginger compositions had detectable spice flavor.

EXAMPLE 6

This example illustrates the preparation compositions of either blanched or unblanched ginger puree mixed at a level of 1% or 2% with Yellow Stone carrot puree.

Sample TK186A (1% Blanched)

Yellow Stone carrots were washed, peeled, blanched, diced and frozen. Two thousand five hundred grams of frozen Yellow Stone carrot dices were cooked in a pressure cooker at 15 p.s.i.g. for five minutes. The cooked dices were then placed in a food blender, 375 grams of water were added and the carrots and water were blended until smooth.

Fresh ginger root was blanched as described in Example 2. The blanched ginger root was then cut into chunks, placed in a blender and blended into a smooth puree.

Nine hundred and ninety grams of hot carrot puree were weighed into a container. Ten grams of blanched ginger puree were mixed with the carrot puree. Portions at a temperature of not less than 150° F. were placed in 4 ounce glass jars and further processed in a conventional fashion and as further required by 21 C.F.R. §113 et seq. The resulting composition was coded TK186A.

TK186B (1% Unblanched)

Fresh ginger root was washed with water and then cut into chunks. The chunks were placed in a blender and made into a smooth puree. Nine hundred and ninety grams of hot carrot puree prepared as described above were weighed into a container. Ten grams of unblanched ginger puree were mixed with the carrot puree. Portions at a temperature of not less than 150° F. were placed in 4 ounce glass jars and further processed in a conventional fashion and as further required by 21 C.F.R. §113 et seq. The resulting composition was coded TK186B.

TK186C (2% Blanched)

Yellow Stone Carrot puree and blanched ginger puree were prepared as described above. Nine hundred and eighty grams of hot carrot puree were weighed into a container. Twenty grams of blanched ginger puree were then mixed with the carrot puree. Portions at a temperature of not less than 150° F. were placed in 4 ounce glass jars and further processed in a conventional fashion and as further required by 21 C.F.R. §113 et seq. The resulting composition was coded TK186C.

TK186D (2% Unblanched)

Yellow Stone carrot puree and unblanched ginger puree were prepared as described above. Nine hundred and eighty grams of hot carrot puree were weighed into a container. Twenty grams of unblanched ginger puree were then mixed with the carrot puree. Portions at a temperature of not less than 150° F. were placed in 4 ounce glass jars and further processed in a conventional fashion and as further required by 21 C.F.R. §113 et seq. The resulting composition was coded TK186D.

Product development specialists tasted Samples TK186A, TK186B, TK186C and TK186C. The TK186A sample containing 1% blanched ginger sample was preferred. The specialists noted that samples TK186B (1% unblanched ginger), TK186C (2% blanched ginger) and TK186C (2% unblanched ginger) all had a strong bite.

EXAMPLE 7

This example illustrates a method that can be used to eliminate any remaining citrus, lemony character of a baby-food compositions containing 0.5% or 1% ginger puree mixed with either apple puree or yellow carrot puree.

Blanched ginger puree is prepared as described in Example 2 or obtained from a commercial source. For 1% ginger compositions, ten grams of the blanched ginger puree is freeze dried using methods known in the art. This results in the removal of the volatile ginger oils which are responsible for the citrus, lemony character of the ginger (Govidarajan, supra, Govindarajan, *CRC Crit. Rev. Food Sci. and Nutr.* 17:189–258, 1983; Mathew et al, *Flavour Ind.* 4:226, 1973). The remaining freeze dried ginger from which the volatile oils have been removed is then added to 990 grams of apple puree prepared as in Example 4 or 990 grams of Yellow Stone carrots prepared as in Example 6 and water added to 1000 grams. For 0.5% ginger compositions, 100 grams of the 1% ginger-containing apple puree or carrot puree composition is mixed with 100 grams of apple puree or carrot puree, respectively. Portions of the ginger-containing apple puree or carrot puree composition, at a temperature of not less than 150° F., are placed in 4 ounce glass jars as described in Example 4 or Example 6 above. The compositions are then tested to determine the taste profile.

EXAMPLE 8

This example illustrates a testing procedure that could be used to determine the beneficial effects of baby-food compositions containing ginger on gastroesophageal reflux.

Spitting up in young infants can be used as a measure of the presence of gastroesophageal reflux. Such spitting up by the infant can be monitored in a daily parental diary in which the parent records the number of episodes of spitting up each day. Full term infants from 4 months to 12 months of age would be considered for entry into the study. General data on the infants would be obtained such as age, weight, length and head circumference and recorded for each infant. Prior to the start of the study, the infants would be thoroughly examined by a physician.

After obtaining informed consent from the parents, the babies would be screened for entry into the study, in an initial one-week observation period. During this period, the parents would record the number of times a day that the baby spits up. Those babies spitting up an average of two or more times a day would then be enrolled in the experimental portion of the study.

The experimental portion of the study would involve a double-blind, cross-over study using two groups of babies with about 10 infants in each group. For one week, each of the two groups would be fed one jar a day of baby-food composition. One group would receive a control composition, such as a vegetable composition of pureed carrots or a fruit composition of apple puree, which does not contain ginger and the second group would receive the test composition of the same pureed baby-food composition which in addition contains ginger. This would then be followed by a one-week "washout" period in which no special food is fed to the infants. The groups would then be crossed over for a one-week period in which the group initially receiving the control baby-food composition in absence of ginger would receive the test baby-food containing the ginger and the group initially receiving the test baby-food composition containing ginger would receive the control baby-food composition containing no ginger.

The daily parental diary would be maintained for the entire study duration. In addition, the parent would record acceptability and tolerance to the baby-food composition including amount offered, amount consumed and any amount refused by the babies.

At the conclusion of the test, statistical analyses would be performed on the resulting data and differences between the two baby-food compositions compared.

All references cited in this specification are hereby incorporated by reference. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results attained.

As various changes could be made in the above methods and compositions without department from the scope of the invention, it is intended that all matter contained in the above description and shown in the accompanying drawings shall be interpreted as illustrative and not in a limiting sense.

What is claimed is:

1. A method for reducing passive regurgitation in an infant comprising feeding to the infant a composition containing an amount of blanched ginger puree effective in reducing passive regurgitation in an acceptable baby-food formulation.

2. The method according to claim 1 wherein the composition contains from about 0.1% to about 0.5% (w/w) blanched ginger puree.

3. The method according to claim 2 wherein the composition further comprises one or more fruits or a vegetables.

4. The method according to claim 3 wherein the fruit is selected from the group consisting of apple, guava, papaya, pineapple, raspberry, strawberry, grape, grapefruit, cherry, orange, banana, pear, cranberry, blueberry, peach, olive, coconut, blackberry, mulberry, fig, prune, lemon, lime, date, pomegranate, apricot, mango, avocados, kiwi, nectarine, raisins, plum, and combinations thereof.

5. The method according to claim 3 wherein the fruit comprises apple puree.

6. The method according to claim 3 wherein the vegetable is selected from the group consisting of buckwheat, rhubarb, sorrel, beets, spinach, Swiss chard, cantaloupe, casaba, cucumber honeydew, pumpkin, summer squash, winter squash, watermelon, barley, corn, hominy, millet, oat, rice, rye, sorghum, sugar cane, wheat, aloe, asparagus, chives, garlic, leek, onion, sarsaparilla, shallot, cottonseed, marshmallow, okra, sweet potato, broccoli, brussel sprouts, cabbage, cauliflower, collards, garden cress, horseradish, kale, kohlrabi, mustard, radish, rutabaga, turnip, watercress, bell pepper, cayenne pepper, paprika, eggplant, white potato, tomato, anise, caraway, carrot, celeriac, celery, coriander, dill, fennel, parsley, parsnip, acacia, alfalfa, black-eyed pea, broad bean, carob bean, chick pea, common beans, green beans, lentil, licorice, lima bean, mesquite, pea, peanut, tamarind, tragacanth, and combinations thereof.

7. The method according to claim 6 wherein the vegetable comprises a yellow carrot puree.

8. A baby-food composition comprising 0.01% to 1% blanched ginger puree and one or more fruits or vegetables in an acceptable baby-food formulation.

9. The baby-food composition according to claim 8 wherein the composition contains from about 0.1% to about 0.5% blanched ginger puree.

10. The composition according to claim 8 wherein the fruit is selected from the group consisting of apple, guava, papaya, pineapple, raspberry, strawberry, grape, grapefruit, cherry, orange, banana, pear, cranberry, blueberry, peach, olive, coconut, blackberry, mulberry, fig, prune, lemon, lime, date, pomegranate, apricot, mango, avocados, kiwi, nectarine, raisins, plum, and combinations thereof.

11. The composition according to claim 10 wherein the fruit comprises apple puree.

12. The composition according to claim 8 wherein the vegetable is selected from the group consisting of buckwheat, rhubarb, sorrel, beets, spinach, Swiss chard, cantaloupe, casaba, cucumber honeydew, pumpkin, summer squash, winter squash, watermelon, barley, corn, hominy, millet, oat, rice, rye, sorghum, sugar cane, wheat, aloe, asparagus, chives, garlic, leek, onion, sarsaparilla, shallot, cottonseed, marshmallow, okra, sweet potato, broccoli, brussel sprouts, cabbage, cauliflower, collards, garden cress, horseradish, kale, kohlrabi, mustard, radish, rutabaga, turnip, watercress, bell pepper, cayenne pepper, paprika, eggplant, white potato, tomato, anise, caraway, carrot, celeriac, celery, coriander, dill, fennel, parsley, parsnip, acacia, alfalfa, black-eyed pea, broad bean, carob bean, chick pea, common beans, green beans, lentil, licorice, lima bean, mesquite, pea, peanut, tamarind, tragacanth, and combinations thereof.

13. The composition according to claim 12 wherein the vegetable comprises a yellow carrot puree.

14. The baby-food composition according to claim 8 wherein the composition possesses chunky components which will pass through a ⅜ inch screen.

15. A method for manufacturing a baby-food product comprising blanching ginger rhizome, pureeing the blanched ginger rhizome and formulating the puree at 0.1% to about 1% in an acceptable baby-food formulation.

16. The method according to claim 15 wherein the formulation contains from about 0.1% to about 0.5% blanched ginger puree.

17. The method according to claim 16 wherein the formulation further comprises one or more fruits or vegetables.

18. The method according to claim 17 wherein the fruit is selected from the group consisting of apple, guava, papaya, pineapple, raspberry, strawberry, grape, grapefruit, cherry, orange, banana, pear, cranberry, blueberry, peach, olive, coconut, blackberry, mulberry, fig, prune, lemon, lime, date, pomegranate, apricot, mango, avocados, kiwi, nectarine, raisins, plum, and combinations thereof.

19. The method according to claim 18 wherein the fruit comprises apple puree.

20. The method according to claim 18 wherein the vegetable is selected from the group consisting of buckwheat, rhubarb, sorrel, beets, spinach, Swiss chard, cantaloupe, casaba, cucumber honeydew, pumpkin, summer squash, winter squash, watermelon, barley, corn, hominy, millet, oat, rice, rye, sorghum, sugar cane, wheat, aloe, asparagus, chives, garlic, leek, onion, sarsaparilla, shallot, cottonseed, marshmallow, okra, sweet potato, broccoli, brussel sprouts, cabbage, cauliflower, collards, garden cress, horseradish, kale, kohlrabi, mustard, radish, rutabaga, turnip, watercress, bell pepper, cayenne pepper, paprika, eggplant, white potato, tomato, anise, caraway, carrot, celeriac, celery, coriander, dill, fennel, parsley, parsnip, acacia, alfalfa, black-eyed pea, broad bean, carob bean, chick pea, common beans, green beans, lentil, licorice, lima bean, mesquite, pea, peanut, tamarind, tragacanth, and combinations thereof.

21. The method according to claim 20 wherein the vegetable comprises a yellow carrot puree.

\* \* \* \* \*